(12) United States Patent
Blaustein et al.

(10) Patent No.: US 6,952,854 B2
(45) Date of Patent: Oct. 11, 2005

(54) COMPLEX MOTION TOOTHBRUSH

(75) Inventors: Lawrence A. Blaustein, Moreland Hills, OH (US); Douglas A. Gall, Strongsville, OH (US); Patrick W. Brown, Auburn, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2 days.

(21) Appl. No.: 10/927,845

(22) Filed: Aug. 27, 2004

(65) Prior Publication Data

US 2005/0005375 A1 Jan. 13, 2005

Related U.S. Application Data

(63) Continuation of application No. 10/676,955, filed on Oct. 1, 2003, which is a continuation of application No. 10/367,373, filed on Feb. 13, 2003, which is a continuation of application No. 09/993,167, filed on Nov. 6, 2001, now Pat. No. 6,725,490.

(51) Int. Cl.⁷ ............................................... A61C 17/22
(52) U.S. Cl. ........................................... 15/22.1; 15/28
(58) Field of Search ................................ 15/22.1, 22.2, 15/22.4, 28, 29

(56) References Cited

U.S. PATENT DOCUMENTS

| | | |
|---|---|---|
| 164,353 A | 6/1875 | Wayne |
| 793,587 A | 6/1905 | Johnson |
| 1,517,320 A | 12/1924 | Stoddart |
| 1,557,244 A | 10/1925 | Domingue |
| 1,712,579 A | 5/1929 | Nichols |
| 1,911,973 A | 5/1933 | Ruse |
| 1,945,616 A | 2/1934 | Mastrud |
| 2,044,863 A | 6/1936 | Sticht |
| 2,140,307 A | 12/1938 | Belaschk et al. |
| 2,172,624 A | 9/1939 | Robert |
| 2,250,975 A | 7/1941 | Sussman |
| 2,435,421 A | 2/1948 | Blair |
| 2,682,066 A | 6/1954 | Keely |
| 2,799,878 A | 7/1957 | Brausch |
| 3,142,852 A | 8/1964 | Phaneuf et al. |
| 3,160,902 A | 12/1964 | Aymar |

(Continued)

FOREIGN PATENT DOCUMENTS

| | | |
|---|---|---|
| AU | 674534 | 3/1994 |
| AU | 706536 | 1/1997 |

(Continued)

OTHER PUBLICATIONS

Bader, "Review of Currently Available Battery–Operated Toothbrushers", *Compend. Contin. Educ. Dent.*, vol. 13, No. 12, p. 1162, 1164–1169.

Photographs of electric toothbrush of BioBrush Industries (22 photographs).

*Primary Examiner*—Mark Spisich
(74) *Attorney, Agent, or Firm*—James C. Vago; Richard L. Alexander

(57) ABSTRACT

A detachable head for use with an electric toothbrush is provided. The electric toothbrush has a handle with a motor disposed therein. The electric toothbrush also has a head which has a longitudinal axis, and a neck disposed between the head and handle. The head has a first bristle holder and a second bristle holder, each having a plurality of bristle tufts. The motor is operatively connected to the first bristle holder to oscillate the first bristle holder about a first axis passing through the first bristle holder generally perpendicular to the longitudinal axis of the head. The motor is also operatively connected to the second bristle holder to oscillate the second bristle holder about a second axis transverse to the longitudinal axis of the head. The second axis is at an end portion of the second bristle holder.

20 Claims, 8 Drawing Sheets

U.S. PATENT DOCUMENTS

| | | |
|---|---|---|
| 3,178,754 A | 4/1965 | Cleverdon |
| 3,379,906 A | 4/1968 | Spohr |
| 3,400,417 A | 9/1968 | Moret |
| 3,588,936 A | 6/1971 | Duve |
| 3,851,984 A | 12/1974 | Crippa |
| 4,048,690 A | 9/1977 | Wolfson |
| 4,156,620 A | 5/1979 | Clemens |
| 4,189,801 A | 2/1980 | Lanusse |
| 4,344,202 A | 8/1982 | Hayat |
| 4,365,376 A | 12/1982 | Oda et al. |
| 4,397,055 A | 8/1983 | Cuchiara |
| 4,420,851 A | 12/1983 | Wiener |
| 4,450,599 A | 5/1984 | Scheller et al. |
| 4,506,400 A | 3/1985 | Klein |
| 4,545,087 A | 10/1985 | Nahum |
| 4,603,448 A | 8/1986 | Middleton |
| 4,698,869 A | 10/1987 | Mierau et al. |
| 4,766,630 A | 8/1988 | Hegemann |
| 4,795,347 A | 1/1989 | Maurer |
| 4,845,795 A | 7/1989 | Crawford et al. |
| 4,880,382 A | 11/1989 | Moret et al. |
| 4,974,278 A | 12/1990 | Hommann |
| 5,000,684 A | 3/1991 | Odrich |
| 5,020,179 A | 6/1991 | Scherer |
| 5,033,150 A | 7/1991 | Gross et al. |
| 5,035,020 A | 7/1991 | Winiewski |
| 5,068,939 A | 12/1991 | Holland |
| 5,070,567 A | 12/1991 | Holland |
| 5,071,348 A | 12/1991 | Woog |
| 5,088,145 A | 2/1992 | Whitefield |
| 5,120,225 A | 6/1992 | Amit |
| 5,138,734 A | 8/1992 | Chung |
| 5,148,567 A | 9/1992 | Daub |
| 5,184,368 A | 2/1993 | Holland |
| 5,253,382 A | 10/1993 | Beny |
| 5,274,870 A | 1/1994 | Stollman |
| 5,283,921 A | 2/1994 | Ng |
| 5,301,381 A | 4/1994 | Klupt |
| 5,311,633 A | 5/1994 | Herzog et al. |
| 5,321,866 A | 6/1994 | Klupt |
| 5,337,435 A | 8/1994 | Krasner et al. |
| 5,353,460 A | 10/1994 | Bauman |
| 5,365,624 A | 11/1994 | Berns |
| 5,378,153 A | 1/1995 | Giuliani et al. |
| 5,381,576 A | 1/1995 | Hwang |
| 5,383,242 A | 1/1995 | Bigler et al. |
| 5,416,942 A | 5/1995 | Baldacci et al. |
| 5,448,792 A | 9/1995 | Wiedemann et al. |
| 5,461,744 A | 10/1995 | Merbach |
| 5,465,444 A | 11/1995 | Bigler et al. |
| 5,467,495 A | 11/1995 | Boland et al. |
| 5,493,747 A | 2/1996 | Inakagata et al. |
| 5,500,970 A | 3/1996 | Maurer et al. |
| 5,504,959 A | 4/1996 | Yukawa et al. |
| 5,504,961 A | 4/1996 | Yang |
| 5,524,312 A * | 6/1996 | Tan et al. .................. 15/22.1 |
| 5,577,285 A | 11/1996 | Drossler |
| 5,590,434 A | 1/1997 | Imai |
| 5,613,259 A | 3/1997 | Craft et al. |
| 5,617,603 A * | 4/1997 | Mei ........................ 15/22.1 |
| 5,651,157 A | 7/1997 | Hahn |
| 5,700,146 A | 12/1997 | Kucar |
| 5,732,433 A * | 3/1998 | Gocking et al. .............. 15/28 |
| 5,822,821 A | 10/1998 | Sham |
| RE35,941 E | 11/1998 | Stansbury, Jr. |
| 5,836,030 A | 11/1998 | Hazeu et al. |
| 5,839,148 A | 11/1998 | Volpenhein |
| 5,842,244 A | 12/1998 | Hilfinger |
| 5,842,245 A * | 12/1998 | Pai ......................... 15/22.1 |
| 5,862,559 A | 1/1999 | Hunter |
| 5,867,856 A | 2/1999 | Herzog |
| 5,901,397 A | 5/1999 | Hafele |
| 5,934,908 A | 8/1999 | Woog et al. |
| 5,974,613 A | 11/1999 | Herzog |
| 5,974,615 A | 11/1999 | Schwarz-Hartmann et al. |
| 6,021,538 A | 2/2000 | Kressner et al. |
| 6,032,313 A | 3/2000 | Tsang |
| 6,047,429 A | 4/2000 | Wu |
| 6,058,541 A | 5/2000 | Masterman et al. |
| 6,092,252 A | 7/2000 | Fischer et al. |
| 6,094,768 A | 8/2000 | Hugon et al. |
| 6,094,769 A | 8/2000 | Driesen et al. |
| 6,141,819 A | 11/2000 | Driesen et al. |
| 6,164,967 A | 12/2000 | Sale et al. |
| 6,195,828 B1 | 3/2001 | Fritsch |
| 6,220,772 B1 | 4/2001 | Taylor |
| 6,233,773 B1 | 5/2001 | Karge et al. |
| 6,237,178 B1 | 5/2001 | Kramer |
| 6,308,358 B2 | 10/2001 | Gruber |
| 6,349,442 B1 | 2/2002 | Cohen |
| 6,363,565 B1 | 4/2002 | Paffrath |
| 6,367,108 B1 | 4/2002 | Fritsch et al. |
| 6,453,499 B1 | 9/2002 | Leuermann |
| 6,574,820 B1 * | 6/2003 | DePuydt et al. ................ 15/28 |
| 6,626,398 B1 | 9/2003 | Cox et al. |
| 6,725,490 B2 | 4/2004 | Blaustein et al. |
| 6,760,946 B2 | 7/2004 | DePuydt |
| 2002/0138926 A1 | 10/2002 | Brown, Jr. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0084528 A1 | 5/2003 | Chan et al. |
| 2003/0126699 A1 | 7/2003 | Blaustein et al. |
| 2003/0140437 A1 | 7/2003 | Eliav |
| 2003/0154567 A1 | 8/2003 | Drossler |
| 2003/0154568 A1 | 8/2003 | Boland et al. |
| 2003/0163882 A1 | 9/2003 | Blaustein et al. |
| 2003/0182744 A1 | 10/2003 | Fattori |
| 2003/0182747 A1 | 10/2003 | Depuydt |
| 2003/0226223 A1 | 12/2003 | Chan et al. |
| 2004/0060132 A1 | 4/2004 | Gatzemeyer |
| 2004/0060137 A1 | 4/2004 | Eliav |
| 2004/0084063 A1 | 5/2004 | Vago |
| 2004/0088806 A1 | 5/2004 | DePuydt |

FOREIGN PATENT DOCUMENTS

| | | |
|---|---|---|
| AU | 708018 | 2/1998 |
| AU | 199948829 | 4/2000 |
| AU | 733458 | 3/2001 |
| AU | 200118387 | 4/2001 |
| CN | 2271352 | 7/1996 |
| CN | 2271353 | 10/1996 |
| CN | 2274947 | 12/1996 |
| CN | 2324987 | 6/1999 |
| CN | 2324988 | 6/1999 |
| DE | 2654853 | 6/1978 |
| DE | 2901136 | 3/1982 |
| DE | 8426426 | 3/1985 |
| DE | 3544256 | 8/1987 |
| DE | 9006097 | 9/1990 |
| DE | 9001258 | 7/1991 |
| DE | 4003305 | 8/1991 |
| DE | 4201873 | 5/1993 |
| DE | 4139788 | 6/1993 |
| DE | 4243220 | 6/1994 |
| DE | 4243221 | 6/1994 |
| DE | 4313970 | 11/1994 |
| DE | 4412301 | 10/1995 |
| DE | 19520303 | 12/1996 |
| DE | 29517610 | 4/1997 |
| DE | 19701964 | 7/1998 |

| | | | | | |
|---|---|---|---|---|---|
| DE | 29821121 | 4/1999 | JP | 6-189822 | 7/1994 |
| DE | 29821331 | 4/1999 | JP | 6-245819 | 9/1994 |
| DE | 19802904 | 7/1999 | JP | 7-116020 | 5/1995 |
| DE | 19803311 | 8/1999 | JP | 7-116021 | 5/1995 |
| DE | 10208529 | 10/2003 | JP | 7-116023 | 5/1995 |
| EP | 098275 | 11/1985 | JP | 7-116024 | 5/1995 |
| EP | 110327 | 5/1987 | JP | 7-148020 | 6/1995 |
| EP | 259648 | 3/1988 | JP | 7-505814 | 6/1995 |
| EP | 560758 | 9/1990 | JP | 7-213343 | 8/1995 |
| EP | 435329 | 12/1990 | JP | 7-93892 | 10/1995 |
| EP | 208401 | 5/1991 | JP | 8-356 | 1/1996 |
| EP | 254397 | 7/1991 | JP | 8-103330 | 4/1996 |
| EP | 0488971 | 6/1992 | JP | 8-103331 | 4/1996 |
| EP | 357863 | 7/1992 | JP | 2511226 | 7/1996 |
| EP | 585738 | 8/1993 | JP | 8-224259 | 9/1996 |
| EP | 569606 | 11/1993 | JP | 8-299372 | 11/1996 |
| EP | 628291 | 5/1994 | JP | 8-322641 * | 12/1996 |
| EP | 651978 | 10/1994 | JP | 2719556 | 11/1997 |
| EP | 691107 | 1/1996 | JP | 10-66704 * | 3/1998 |
| EP | 374152 | 4/1996 | JP | 2565618 | 3/1998 |
| EP | 537465 | 4/1996 | JP | 10-507375 | 7/1998 |
| EP | 546203 | 8/1996 | JP | 10-507671 | 7/1998 |
| EP | 0 744 139 | 11/1996 | JP | 2811246 | 8/1998 |
| EP | 689404 | 5/1997 | JP | 2804940 | 9/1998 |
| EP | 624079 | 7/1997 | JP | 11-503042 | 3/1999 |
| EP | 520985 | 8/1997 | JP | 11-505742 | 5/1999 |
| EP | 652733 | 11/1997 | JP | 11-235234 | 8/1999 |
| EP | 641181 | 12/1998 | JP | 11-513922 | 11/1999 |
| EP | 977521 | 2/2000 | JP | 6-245820 | 1/2000 |
| EP | 990424 | 4/2000 | JP | 3069418 | 7/2000 |
| EP | 1053721 | 11/2000 | JP | 5-146314 | 7/2000 |
| EP | 1132057 A1 | 9/2001 | KR | 1984-0004668 | 9/1984 |
| EP | 1256327 | 11/2002 | KR | 1986-0001137 | 6/1986 |
| FR | 1121618 | 8/1956 | KR | 1990-009574 | 6/1990 |
| FR | 1271022 | 7/1961 | KR | 1990-0007365 | 6/1990 |
| FR | 1525112 | 5/1968 | KR | 1991-700015 | 8/1990 |
| FR | 2368854 | 5/1978 | KR | 1994-0013418 | 7/1994 |
| GB | 452961 | 9/1936 | KR | 1995-0002814 | 2/1995 |
| GB | 500517 | 2/1939 | KR | 1995-0010820 | 5/1995 |
| GB | 914844 | 1/1963 | KR | 1997-0000408 | 1/1997 |
| GB | 989953 | 4/1965 | KR | 1997-0000409 | 1/1997 |
| GB | 1008530 | 10/1965 | KR | 1995-0024551 | 4/1998 |
| GB | 1070637 | 6/1967 | KR | 1999-0044511 | 6/1999 |
| GB | 1098893 | 1/1968 | KR | 1999-0041729 | 4/2000 |
| GB | 1240438 | 7/1971 | KR | 2000-0006046 | 4/2000 |
| GB | 1307887 | 2/1973 | KR | 1999-0028614 | 5/2000 |
| GB | 2029926 | 3/1980 | NZ | 510666 | 3/2001 |
| GB | 2036551 | 7/1980 | NZ | 511820 | 5/2001 |
| GB | 1583558 | 1/1981 | NZ | 337972 | 9/2001 |
| GB | 2228861 | 9/1990 | SU | 1752336 A1 | 5/1990 |
| GB | 2237505 | 5/1991 | TW | 96609 | 6/1976 |
| GB | 2247297 * | 2/1992 | TW | 148155 | 11/1978 |
| GB | 2290224 | 12/1995 | TW | 148156 | 11/1978 |
| GB | 2319170 | 5/1998 | TW | 164493 | 7/1979 |
| GB | 2371217 | 7/2002 | TW | 178744 | 5/1980 |
| GB | 3004958 | 7/2002 | TW | 200663 | 5/1981 |
| JP | 40-8743 | 8/1965 | TW | 229411 | 5/1982 |
| JP | 57-89810 | 6/1982 | TW | 273146 | 7/1982 |
| JP | 63-168108 | 7/1988 | TW | 248031 | 12/1982 |
| JP | 2-19241 | 2/1990 | TW | 239963 | 3/1983 |
| JP | 2-218309 | 8/1990 | TW | 233472 | 5/1983 |
| JP | 4-133733 | 7/1991 | TW | 249332 | 6/1983 |
| JP | 5-137615 | 6/1993 | TW | 228087 | 11/1983 |
| JP | 5-146313 | 6/1993 | TW | 274724 | 4/1984 |
| JP | 5-161509 | 6/1993 | TW | 311444 | 12/1985 |
| JP | 5-199917 | 8/1993 | TW | 339233 | 4/1986 |
| JP | 5-199918 | 8/1993 | TW | 256049 | 1/1993 |
| JP | 5-269023 | 10/1993 | TW | 238504 | 6/1993 |
| JP | 6-47298 | 2/1994 | TW | 212909 | 9/1993 |
| JP | 6121710 | 5/1994 | TW | 294031 | 11/1994 |
| JP | 3-1895 | 6/1994 | TW | 239964 | 2/1995 |

| | | | | | | |
|---|---|---|---|---|---|---|
| TW | 253174 | 8/1995 | | WO | WO 97/25899 | 7/1997 |
| TW | 281884 | 7/1996 | | WO | WO 97/28757 | 8/1997 |
| TW | 137856 | 12/1997 | | WO | WO 97/34545 | 9/1997 |
| TW | 330410 | 4/1998 | | WO | WO 97/43923 | 11/1997 |
| TW | 330411 | 4/1998 | | WO | WO 98/00049 | 1/1998 |
| TW | 334345 | 6/1998 | | WO | WO 98/01083 | 1/1998 |
| TW | 406557 | 9/2000 | | WO | WO 98/14090 | 4/1998 |
| TW | 455298 | 9/2001 | | WO | WO 98/23223 | 6/1998 |
| TW | 455299 | 9/2001 | | WO | WO 98/26729 | 6/1998 |
| WO | WO 83/03956 | 11/1983 | | WO | WO 98/26730 | 6/1998 |
| WO | WO 91/07115 | 5/1991 | | WO | WO 98/46103 | 10/1998 |
| WO | WO 91/13570 | 9/1991 | | WO | WO 98/47444 | 10/1998 |
| WO | WO 92/13499 | 8/1992 | | WO | WO 99/03372 | 1/1999 |
| WO | WO 92/19177 | 11/1992 | | WO | WO 99/12492 | 3/1999 |
| WO | WO 93/09729 | 5/1993 | | WO | WO 99/20202 | 4/1999 |
| WO | WO 93/20777 | 10/1993 | | WO | WO 99/23910 | 5/1999 |
| WO | WO 94/03124 | 2/1994 | | WO | WO 99/37180 | 7/1999 |
| WO | WO 94/03125 | 2/1994 | | WO | WO 99/56660 | 11/1999 |
| WO | WO 94/09676 | 5/1994 | | WO | WO 99/65359 | 12/1999 |
| WO | WO 94/12121 | 6/1994 | | WO | WO 00/15076 | 3/2000 |
| WO | WO 94/21191 | 9/1994 | | WO | WO 00/41592 | 7/2000 |
| WO | WO 94/21193 | 9/1994 | | WO | WO 00/41645 | 7/2000 |
| WO | WO 94/23667 | 10/1994 | | WO | WO 00/56186 | 9/2000 |
| WO | WO 94/28823 | 12/1994 | | WO | WO 00/74522 | 12/2000 |
| WO | WO 95/11636 | 5/1995 | | WO | WO 00/74592 | 12/2000 |
| WO | WO 95/27419 | 10/1995 | | WO | WO 00/78244 | 12/2000 |
| WO | WO 95/33419 | 12/1995 | | WO | WO 01/06946 | 2/2001 |
| WO | WO 96/09018 | 3/1996 | | WO | WO 01/19281 | 3/2001 |
| WO | WO 96/09019 | 3/1996 | | WO | WO 01/32095 | 5/2001 |
| WO | WO 96/13223 | 5/1996 | | WO | WO 01/52696 | 7/2001 |
| WO | WO 96/13224 | 5/1996 | | WO | WO 01/82826 | 11/2001 |
| WO | WO 96/31171 | 10/1996 | | WO | WO 03/043459 A2 | 5/2003 |
| WO | WO 96/37164 | 11/1996 | | WO | WO 03/077790 A1 | 9/2003 |
| WO | WO 97/01307 | 1/1997 | | | | |
| WO | WO 97/19651 | 6/1997 | | | | |
| WO | WO 97/20484 | 6/1997 | | | | |

\* cited by examiner

US 6,952,854 B2

COMPLEX MOTION TOOTHBRUSH

CROSS REFERENCES TO RELATED APPLICATIONS

This is a continuation of application Ser. No. 10/676,955, filed Oct. 1, 2003, which is a continuation of application Ser. No. 10/367,373, filed Feb. 13, 2003, which is a continuation of application Ser. No. 09/993,167, filed Nov. 6, 2001, now U.S. Pat. No. 6,725,490, the substances of which are incorporated herein by reference.

FIELD OF THE INVENTION

The invention is related to the art of electric toothbrushes and detachable heads therefor.

BACKGROUND OF THE INVENTION

Electric toothbrushes having one or more bristle holders are known in the art. However, there is a continuing need to provide electric toothbrushes which can provide improved cleaning by a synergistic combination of a first bristle holder motion and the bristle tuft arrangements of the first and/or second bristle holders.

BRIEF SUMMARY OF THE INVENTION

A detachable head for use with an electric toothbrush is provided. The electric toothbrush has a handle with a motor disposed therein. The electric toothbrush also has a head which has a longitudinal axis, and a neck disposed between the head and handle. The head has a first bristle holder and a second bristle holder, each having a plurality of bristle tufts. The motor is operatively connected to the first bristle holder to oscillate the first bristle holder about a first axis passing through the first bristle holder generally perpendicular to the longitudinal axis of the head. The motor is also operatively connected to the second bristle holder to oscillate the second bristle holder about a second axis transverse to the longitudinal axis of the head. The second axis is at an end portion of the second bristle holder.

BRIEF DESCRIPTION OF THE SEVERAL VIEWS OF THE DRAWINGS

The invention may take form in various components and arrangements of components, and in various procedures and arrangements of procedures. The drawings are only for purposes of illustrating preferred embodiments, they are not to scale, and not to be construed as limiting the invention.

DETAILED DESCRIPTION OF THE INVENTION

Figure 1:
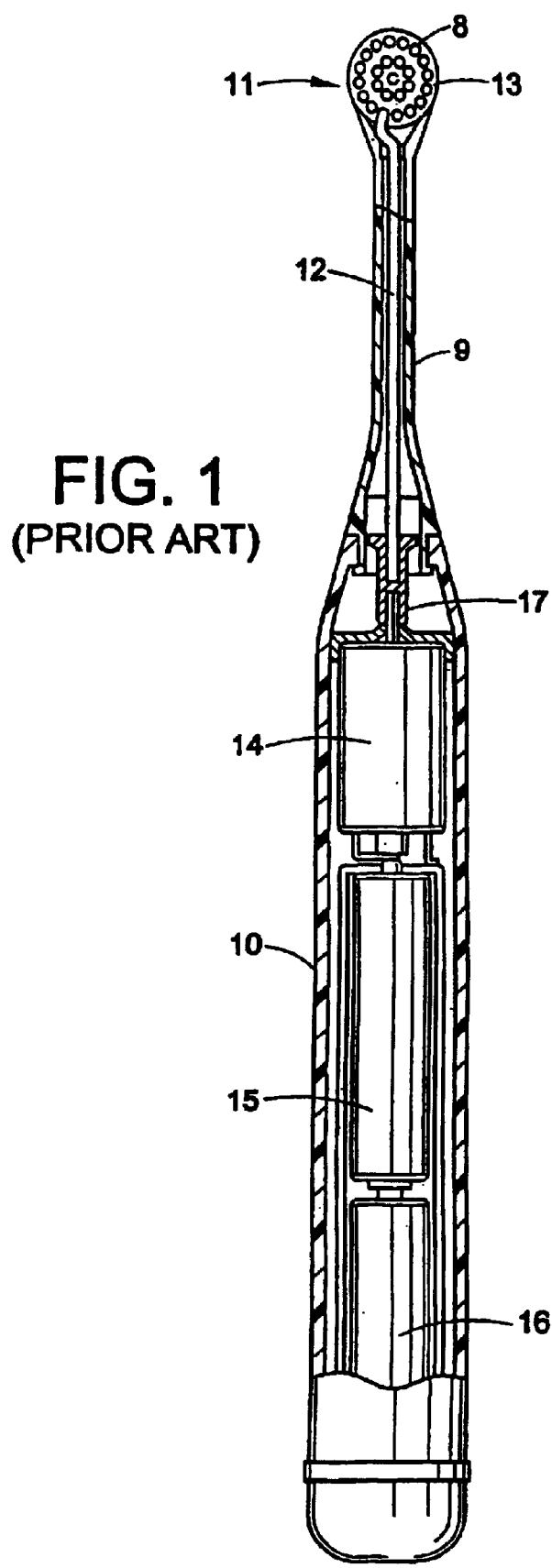
FIG. 1 is a sectional bottom view of a toothbrush.
Figure 4:
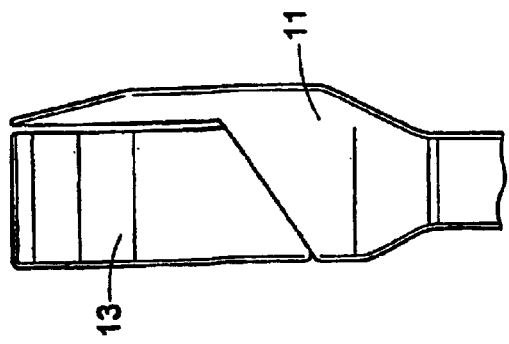
FIG. 4 is an opposite side view of FIG. 2.
Figure 7:
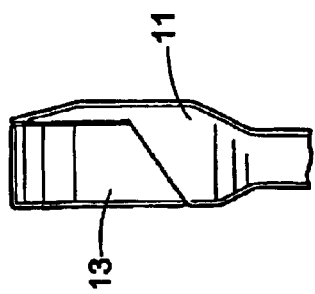
FIGS. 5, 6 and 7 are respectively the same views as FIGS. 2, 3 and 4 of a different toothbrush and to a different scale.

Referring to the drawings, in FIG. 1 the toothbrush comprises a handle 10 at a first end of the toothbrush, a head 11 at a second end of the toothbrush, a neck 9 extending therebetween, a rotatable shaft 12 extending from the handle to the head, and a generally circular bristle holder 13 having a plurality of bristle tufts embedded therein, wherein each tuft 8 comprises a plurality of bristles. The handle provides compartments for holding an electric motor 14 and two batteries 15 and 16, although a rechargeable power source can be substituted for the batteries 15 and 16. A shaft coupling 17 is arranged to grip one end of the shaft 12 and allow the shaft to be pulled out for cleaning or replacement as will be described below.

Figure 2:
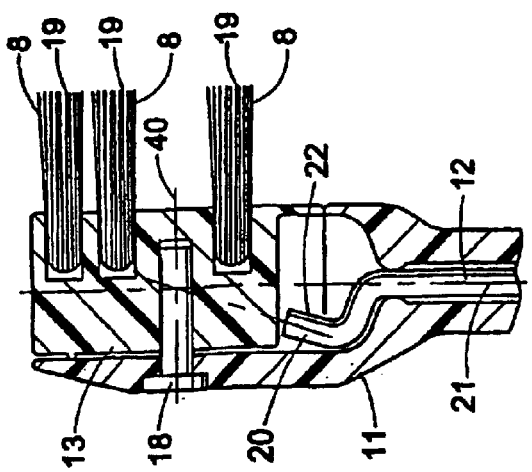
FIG. 2 shows a cross-sectional side view of part of the toothbrush of FIG. 1.

The head 11, as is better seen in FIG. 2, supports a post 18, which provides a rotational or oscillatory pivot axis 40 for the bristle holder 13. Bristles 19 are shown for illustrative purposes only in FIG. 2. The shaft 12 has an integrally formed remote-most end 20 that is offset from a central longitudinal axis 21 of the shaft. The remote-most end 20 fits into a slot 22 (see FIG. 3) formed in a side of the bristle holder 13. It will be noted that the end 20 points towards an intersection of the first axis 21 and the pivot axis 40 of the post 18. In one embodiment, the post is arranged so that the pivot axis 40 is substantially perpendicular to the central longitudinal axis 21 of the shaft. The pivot axis 40 is also substantially parallel to the direction in which the bristles 19 extend. While this arrangement is preferred, it is contemplated that the post 18 can be arranged differently. For example, the post 18 might be angled so that the pivot axis 40 is not substantially perpendicular to the longitudinal axis 21 of the shaft but rather forms an acute angle therewith in order to provide a wobbling or swiveling action about the pivot axis 40. When the shaft 12 is rotated by the motor 14, the remote end 20 describes a circle about the shaft 12 and drivingly engages the slot 22 to cause the bristle holder 13 to vibrate or oscillate about the pivot axis of the bristle holder 13. In this regard, the formed remote-most end 20 may be considered to be a cam or a gear tooth. To vibrate is to move to and fro or from side to side. To oscillate is to move or travel back and forth between two points. A cam is a shaped component or potion of a component, which determines the motion of a follower. As may be seen in FIG. 3, slot 22 is closed-ended and extends radially inward from the outer circumference of the holder to less than the distance to the center of the holder and between adjacent pairs of bristle holes. Thus, the bristle holder 13 pivots, oscillates, or rotates forwards and backwards about the center of the post 18. To pivot is to turn on or as if on a pivot. To rotate is to turn about an axis or a center. Such movement provides a first relative motion between the head 11 and the bristles 19 and is generally beneficial for efficient cleaning of teeth. The width of the slot 22 is preferably generally the same as the diameter of the end 20 to leave minimum play; this keeps noise to a minimum in use.

Figure 5:
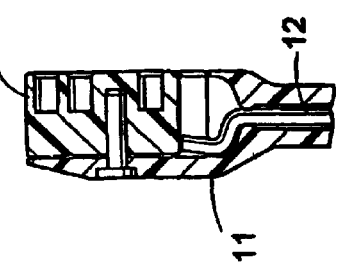

Preferably, the motor 14 runs at around 6000 rpm. Where desired, the motor can run at other speeds or be arranged to run at two or more speeds, selectable by the user. FIG. 1 shows a toothbrush where the holder 13 vibrates, oscillates, or rotates through an angle of 30 degrees. In FIG. 2, the angle is 35 degrees and in FIG. 5 the angle is 15 degrees. It will therefore be appreciated that the rotational angle can be chosen by fitting different shafts 12 and that the same bristle holder can be used for all angles.

Figure 3:
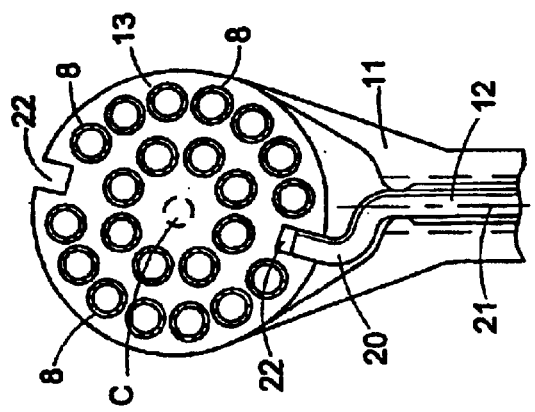
FIG. 3 is a sectional bottom view of FIG. 2.
Figure 6:
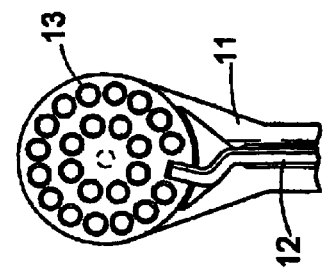

Each bristle holder 13 may be provided with more than one slot 22 as may be seen in FIG. 3, opposite each other so as to be better balanced or so that different slots can be used if the one slot wears or if the bristles wear unevenly in use. In other words, the holder 13 can then be set up in two or more rotational positions. The holder 13 is preferable easily removable from the head 11, by being spring clipped to the post 18 for example. Such removal allows better cleaning and storing in a hygienic container perhaps and also enables the shaft 12 to be readily withdrawn and replaced when required.

The described shafts 12 are preferably integrally formed, i.e., a single length of a thin rod and shaped as shown. However, it is possible to arrange for the remote end or can 20 to be separately formed or provided and fixed to a straight end part of the shaft or elsewhere on the shaft. Such a separate part can be a brush having a central axis coinciding with the axis 21 of the shaft and an off-center driving post. The driving post then takes up the position and function of the remote end or cam 20. Thus, the driving post and the slot 22 then form the driving engagement between the shaft and the holder 13 and so the driving post can be regarded as the remote end of the shaft.

It is also possible, but not usually so convenient, in some embodiments of the invention to arrange for the holder 13 to be hingedly pivoted at one side, for example opposite the shaft. In such a case, bristles mounted nearer the hinged pivot will not actually move as much as bristles at the side next to the shaft but they will still vibrate significantly.

It will also be appreciated that whether pivoted to rotate or to hinge, the bristle holder 13 need not be circular. However, a circular holder 13 is normally preferred so that its rotational position can be changed when desired, as mentioned above.

While the above-described shaft arrangement is preferred, it is contemplated that other shaft arrangements can be used with the present invention. For example, the arrangement described in U.S. Pat. No. 5,732,432, the substance of which is incorporated herein by reference, might be substituted to accommodate mechanical misalignments of the shaft and mechanical strain during use. Further, the head 11 might be provided in a form in which it can be readily detached from the handle 10. This could be accomplished using, coupling arrangements for the shaft and body portion of the head. Such arrangements are known in the art. For example, the head and handle portions can include mating slots, spring clips, and protrusions and/or locking or securing tabs and grooves. The shaft can be divided into two sections, each section including a coupling element. For example the coupling is achieved with a keyed arrangement. For instance, coupling elements can include male and female mating splines affixed to respective shaft section ends, or as shown in U.S. Pat. No. 5,617,601, the substance of which is incorporated herein by reference. Further, the slot 22 might be replaced by a wobble plate, such as described in U.S. Pat. No. 5,784,743, the substance of which is incorporated herein by reference.

Figure 8:
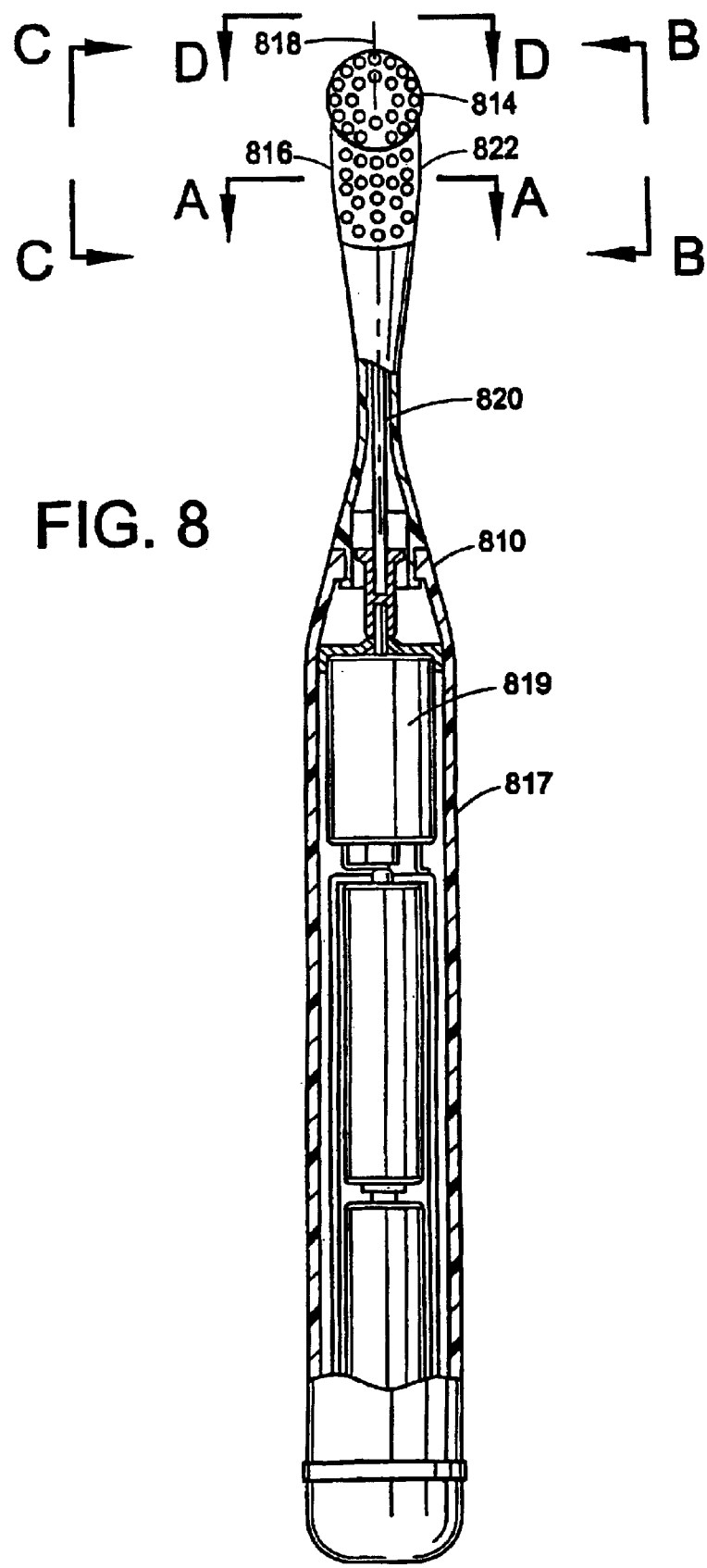
FIG. 8 is a bottom view of an enhanced toothbrush having a second bristle holder. The toothbrush is shown in partial section.
Figure 8A:
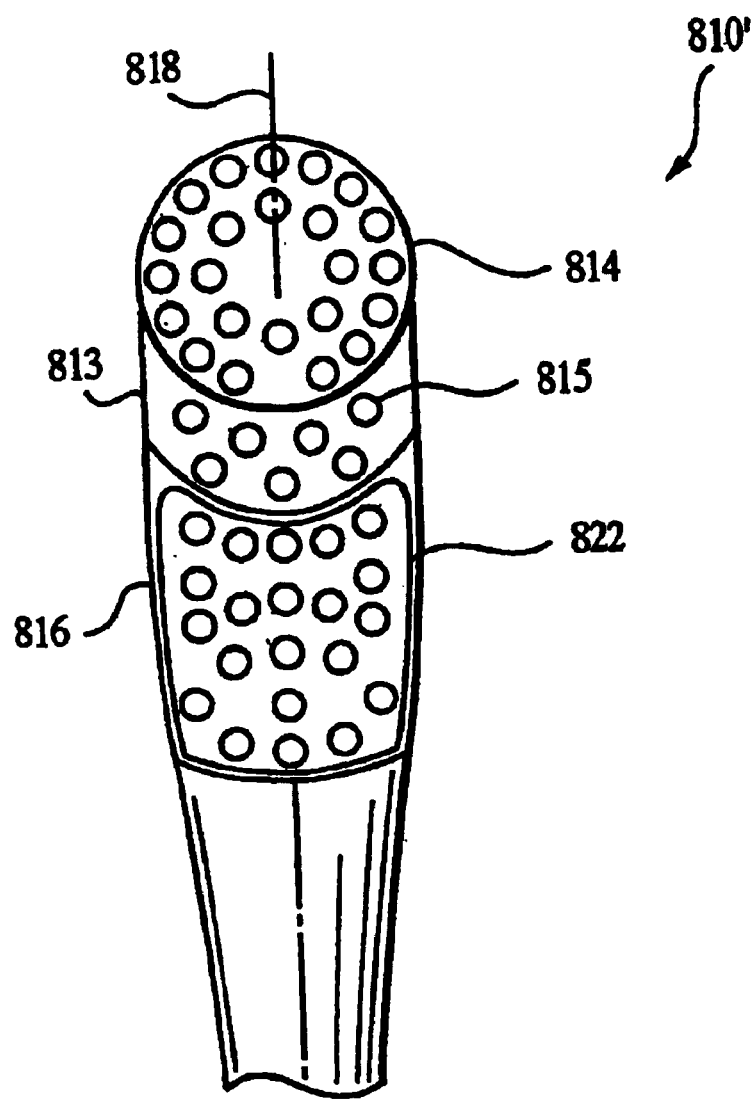

With additional reference now to FIG. 8–FIG. 18, embodiments of an enhanced electric toothbrush 810 include a first bristle holder 814 similar to the bristle holder 13 described above. The enhanced toothbrush 810 has a head 816 and a body or handle 817. Of course, the enhanced toothbrush includes a motor 819 and batteries for powering the motor. The head portion 816 has a longitudinal axis 818. The first bristle holder 814 is illustrated as circular. However, other shape bristle holders are contemplated and within the scope of the invention. The first bristle holder 814 includes at least one slot as described above (see FIG. 3) for receiving a remote-most end or can of a driving shaft 820 as described in reference to FIG. 1–FIG. 7. The remote-most end (see FIG. 3) of the driving shaft is bent or offset from a central longitudinal axis 21 (see FIG. 3) of the driving shaft 820 as described above. The motor 819 is operative to rotate the shaft 820. In short, with regard to the construction and operation of the shaft 820 in relation to the first bristle holder 814, the enhanced toothbrush 810 is similar to the toothbrush described in reference to FIG. 1–FIG. 7. However, embodiments of the enhanced electric toothbrush 810 also include second bristle holders disposed adjacent the first bristle holders, such as second bristle holder 822. While it is desirable to locate the second bristle holder directly adjacent the first bristle holder, it is contemplated that a gap may be provided between the first and second bristle holders. In addition, the space between the movable first and second bristle holders might be filled with stationary or fixed bristles which are embedded in fixed or stationary third bristle holder (See e.g., FIG. 8A) which forms part of the toothbrush head. In many embodiments of the enhanced electric toothbrush, the second bristle holders are movable and separately associated with, and separately driven by, a driving shaft such as the driving shaft 820. The movable second bristle holders are movable in directions and/or manners that are different and distinct from whichever of the rotary or hingedly pivoted vibratory movements, described in reference to FIG. 1–FIG. 7, is used in the particular embodiment.

Figure 9:
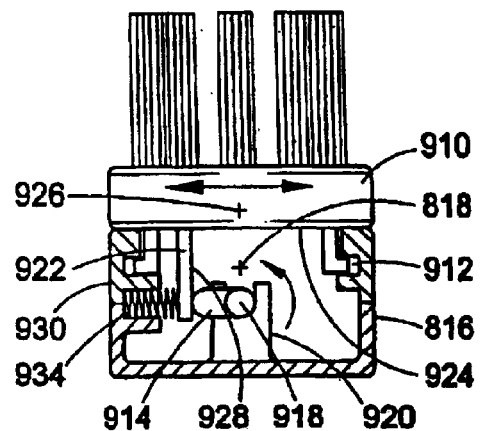
FIG. 9 is a sectional view taken along A—A in FIG. 8 of a first embodiment of a toothbrush head portion.
Figure 9A:
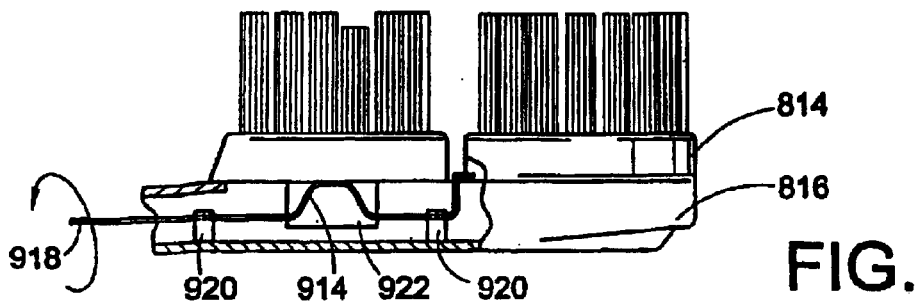
FIG. 9A is a partial sectional side view of the first embodiment.
Figure 12:
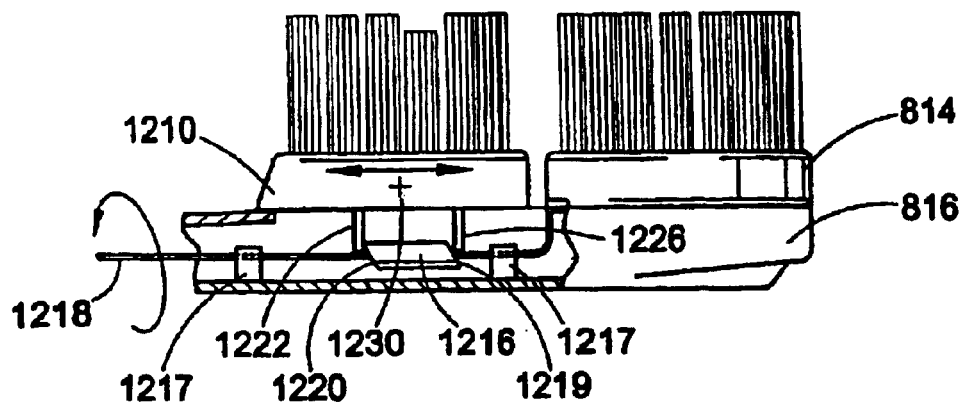
FIG. 12 is a partial sectional view taken along B—B in FIG. 8 of a fourth embodiment of a toothbrush head.
Figure 13:
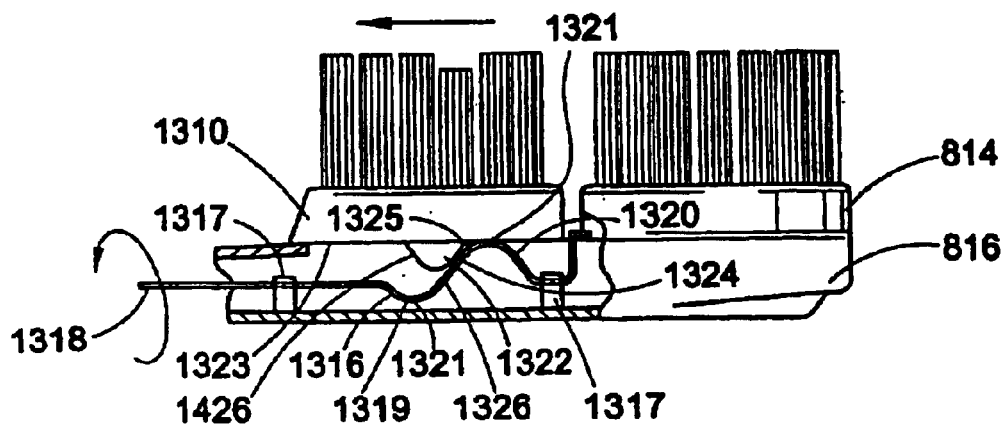
FIG. 13 is a partial sectional view taken along B—B in FIG. 8 of a fifth embodiment of a toothbrush head.
Figure 15:
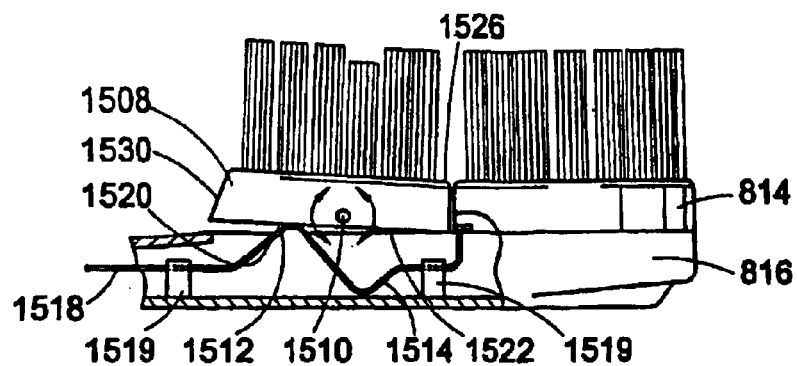
FIG. 15 is a partial sectional view taken along B—B in FIG. 8 of a sixth embodiment of a toothbrush head.

For example, referring to FIG. 9, a second bristle holder 910 is movably mounted in slots 912 in the toothbrush head 816 and separately driven in a vibratory, side-to-side, motion in a direction substantially perpendicular to the direction of the longitudinal axis 818 by an eccentric cam 914 included on a driving shaft 918. The cam 914 and other cams described below can comprise one or more bends in the shaft 918, as shown for example, example in FIG. 9A and as seen in views of other embodiments described below such as seen in FIG. 12, FIG. 13, and FIG. 15. Alternatively, the cam 914 can be provided as a separate piece, which is attached to the shaft 918 by adhesive, a press or snap fit, a co-molding or any other mechanical or chemical means known in the art. Optionally, the driving shaft is supported by a shaft support 920. A cam follower 922 depends from a bottom surface 924 of the second bristle holder 910. The cam follower 922 is offset from a longitudinal axis 926 of the second bristle holder. As the motor 819 of the enhanced toothbrush 810 rotates the shaft 918, the cam 914 comes into contact with a cam contact surface 928 of the cam follower 922 and drives the cam follower 922, and therefore, the second bristle 910 holder toward one side 930 of the enhanced toothbrush 810 and away from the longitudinal axis 818 of the head portion 816. As the shaft 918 continues to rotate, the cam 914 becomes disengaged with the cam follower 922. A resilient biasing member such as a spring 934, lodged between a wall of the head portion 816 and a second surface of the cam follower, urges the cam follower 922, and therefore the second bristle holder 910, back toward the longitudinal axis 818 of the head portion 816. As this back and forth or sided to side motion is repeated (as the shaft 918 continues to rotate), a sweeping or brushing motion is provided that is distinct from and complimentary to the motion provided by the first bristle holder 814. The stroke and/or frequency of the second bristle holder 910 can be changed by varying the construction of the spring and placement and/or sizing of the cam 914 and the cam follower 922. For example, the cam follower 922 might be placed closer to the axis 926 to provide a shorter stroke for the cam follower 922, or a stronger spring might be provided to increase the rate of return of the second bristle holder 910, or more than one spring might be provided. Alternatively, the cam follower 922 might form an acute angle with the bottom surface 924 of the second bristle holder 910 or the first surface can be provided as accurate, curvilinear, or in other complex forms as opposed to the planar surface shown in FIG. 9.

Figure 10:
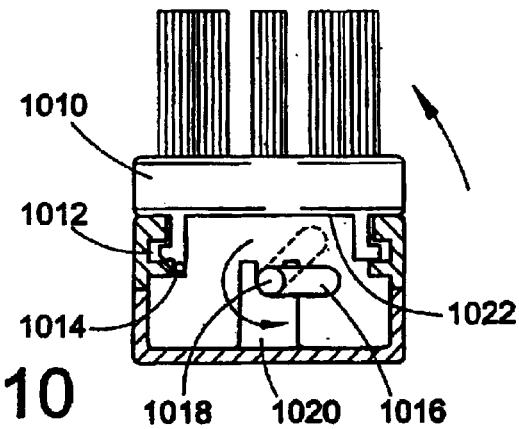
FIG. 10 is a sectional view taken along A—A in FIG. 8 of a second embodiment of a toothbrush head portion.

Referring to FIG. 10, in a second embodiment of the enhanced toothbrush 810 a second bristle holder 1010 is movably mounted in slots 1012 in the toothbrush head 816 and separately driven in a vibratory, swinging or pivoting motion about a hinge or pivot 1014, by a cam 1016 included on a driving shaft 1018. The cam 1016 can comprise one or more bends in the shaft 1018 or be provided as a separate piece as previously discussed. Optionally, the driving shaft is supported by a shaft support 1020. A cam contact surface 1022 is located on a bottom surface of the second bristle holder 1010. As the motor 819 of the enhanced toothbrush 810 rotates the shaft 1018, the cam 1016 comes into contact with the cam contact surface 1022 and drives or pushes the second bristle holder 1010 causing the second bristle holder to swing or pivot about the hinge or pivot 1014. As the shaft 1018 continues to rotate, the cam 1016 becomes disengaged with the cam contact surface 1022. During use, as the cam 1016 comes in contact with the cam contact surface 1022, bristles of the second bristle holder 1010 are urged against the users teeth with greater force. Preferably, bristles of the second bristle holder 1010 are urged between the teeth of the user to provide a cleaning and flossing function. As the cam disengages with the contact surface 1022, bristles pressing against the teeth of the user urge the second bristle holder away from the users teeth. As this swinging or pivoting motion is repeated (as the shaft 1018 continues to rotate), a flossing or deep cleaning motion is provided that is distinct from and complimentary to the motion provided by the first bristle holder 814.

Figure 11:
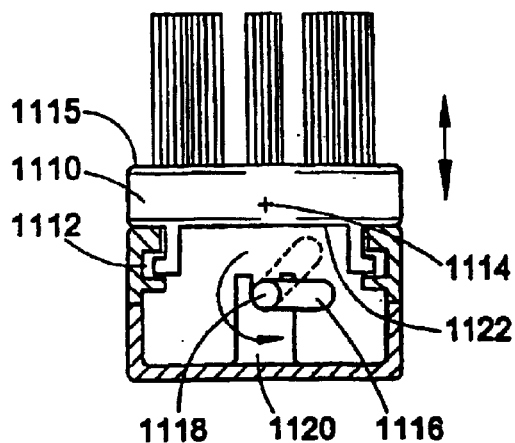
FIG. 11 is a sectional view taken along A—A in FIG. 8 of a third embodiment of a toothbrush head portion.

Referring to FIG. 11, in a third embodiment of the enhanced toothbrush 810 a second bristle holder 1110 is movably mounted in slots 1112 in the toothbrush head 816 and separately driven in a vibratory, lifting or vertical pulsating motion (e.g., in a direction substantially perpendicular to the longitudinal axis 1114 and substantially parallel to a surface 1115 of the second bristle holder 1110 as shown by the way of example in FIG. 11) within the slots 1112, by a cam 1116 included on a driving shaft 1118. Optionally, the driving shaft is supported by a shaft support 1120. The cam 1116 can comprise one or more bends in the shaft 1118 or can be provided as a separate piece as previously discussed. A cam contact surface 1122 is located on a bottom surface of the second bristle holder 1110. As the motor 819 (see FIG. 8) of the enhanced toothbrush 810 rotates the shaft 1118, the cam 1116 comes into contact with the cam contact surface 1122 and drives or lifts, in a vibratory, lifting, or vertical pulsating motion, the second bristle holder 1110 causing the second bristle holder to lift or pulsate in a direction away from the head portion 816 and toward the teeth of a toothbrush user (not shown). As the shaft 118 continues to rotate, the cam 1116 becomes disengaged with the cam contact surface 1122. During use, as the cam 1116 comes in contact with the cam contact surface 1122, bristles of the second bristle holder 1110 are urged against the user's teeth with varying degrees of force. Preferably, bristles of the second bristle holder 1110 are urged between the teeth of the user to provide a cleaning and flossing function. As the cam disengages with the contact surface 1122, bristles pressing against the teeth of the user urge the second bristle holder away from the user's teeth and back toward the head portion 816. As this lifting or vertical pulsating motion is repeated (as the shaft 1118 continues to rotate), a flossing or deep cleaning motion is provided that is distinct from and complimentary to the motion provided by the first bristle holder 814.

Referring to FIG. 12, in a fourth embodiment of the enhanced toothbrush 810 a second bristle holder 1210 is movably mounted in slots (not shown, but similar to the slots 912 illustrated in FIG. 9) in the toothbrush head 816 and separately driven in a reciprocating or translating, longitudinal motion within the slots by a cam 1216 included on a driving shaft 1218. Optionally, the shaft is supported by shaft supports 1217. The shaft supports may include C or U shaped portions (not shown) that are operative to receive and snap around the shaft. Other means for retaining a shaft in a support are known in the art. The cam 1216 can comprise a shaped bead, with an appropriate eccentric configuration, placed or molded over and firmly secured to the shaft 1218. In one embodiment, the cam 1216 includes a pair of acutely angled surfaces 1219, 1220 which are inclined in the same direction and at the same angle of inclination, but which are disposed at opposite ends of the cam 1216. The direction of inclination and angle of inclination can be varied as desired to change the frequency and stroke of the second bristle holder 1210. First 1222 and second 1226 cam followers depend from a bottom surface of the second bristle holder 1210. The cam followers 1222, 1226 are offset or spaced from a transverse axis 1230 of the second bristle holder. The cam followers 1222, 1226 straddle and/or capture the cani 1216 so that the angled surfaces 1219, 1220 slidably engage the free ends of the cam followers 1222 and 1226. As the motor 819 (see FIG. 8) of the enhanced toothbrush 810 rotates the shaft 1218, the first acutely angled surface 1220 of the cam 1216 comes into contact with a surface of the first cam follower 1222 and drives the cam follower, and therefore, the second bristle holder 1210, away from the first bristle holder 814 along the longitudinal axis 818 of the head portion 816. As the shaft 1218 continues to rotate, the cam 1216 becomes disengaged with the first cam follower 1222. The second acutely angled second surface 1219 of the cam 1216 then comes into contact with a surface of the second cam follower 1226 and drives the second cam follower 1226, and therefore, the second bristle holder 1210, back toward the first bristle holder 814. As this back and forth motion is repeated (as the shaft 1218 continues to rotate), a scrubbing action is provided by the reciprocating or translating motion that is distinct from and complimentary to the motion provided by the first bristle holder 814.

Figure 14:
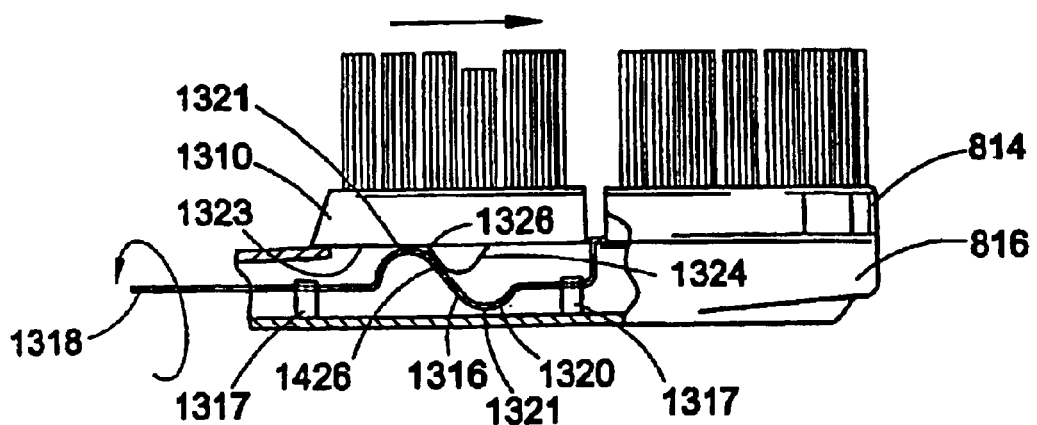
FIG. 14 is a partial sectional view taken along B—B in FIG. 8 of the fifth embodiment of a toothbrush head. A shaft is shown rotated to a different position than shown in FIG. 13.

Referring to FIG. 13 and FIG. 14, in a fifth embodiment of the enhanced toothbrush 810 a second bristle holder 1310 is movably mounted in slots (not shown, but similar to the slots 912 illustrated in FIG. 9) in the toothbrush head 816 and separately driven in an reciprocating or translating, longitudinal motion, by a cam 1316 included on a driving shaft 1318. Optionally, the shaft is supported by shaft supports 1317. The shaft supports may include C or U shaped portions (not shown) that are operative to receive and snap around the shaft. Other means for retaining a shaft in a support are known in the art. The cam 1316 is sinusoidal or curvilinear in nature in that it has one or more adjacent arcuate bends 1319 and 1320 in the shaft 1318. The arcuate bends 1319, 1320 have each have an apex 1321, and the apexes 1321 are disposed on opposite sides of the driving shaft 1318. A cam follower 1322 depends from a bottom surface 1323 of the second bristle holder 1310 and is disposed between the apexes 1321 of the cam 1316. As the motor 819 of the enhanced toothbrush 810 rotates the shaft 1318, a first surface 1325 of the cam 1316 comes into contact with a first surface 1324 of the cam follower 1322 and drives the cam follower 1322, and therefore, the second bristle holder 1310 away from the first bristle holder 814 in a direction along the longitudinal axis 818 of the head portion 816. As the shaft 1318 continues to rotate, the apex 1321 passes and becomes disengaged with the first cam follower surface 1324. A second surface 1326 of the cam 1316 then comes into contact with a second surface 1426 of the cam follower 1322 and the drives the cam follower 1322, and therefore, the second bristle holder 1310 back toward the first bristle holder 814. As this back and forth motion is repeated (as the shaft 1318 continues to rotate), a scrubbing action is provided by the reciprocating or translating motion that is distinct from and complimentary to the motion provided by the first bristle holder 814. The stroke and frequency of the reciprocating or translating motion can be varied by changing the spacing between the apexes and/or the amplitude, shape, or height of the apexes.

Referring to FIG. 15, in a sixth embodiment of the enhanced toothbrush 810, a second bristle holder 1508 is movably mounted to the toothbrush head 816 with a pivot 1510, which can be provided in the form of a pin or hinge. The pivot 1510 is installed at a centrally located transverse axis of the second bristle holder 1508. In one embodiment, the second bristle holder 1508 pivots about a pin, which is anchored in the sidewalls of the toothbrush neck or head 816 at the midpoint of the second bristle holder 1508. The second bristle holder 1508 is separately driven in a vibratory, swinging, teetering or rocking motion by a cam comprised of first 1512 and second 1514 cam portions included on a driving shaft 1518. Optionally, the shaft is supported by shaft supports 1519. The shaft supports may include C or U shaped portions (not shown) that are operative to receive and snap around the shaft. Other means for retaining a shaft in a support are known in the art. The cam portions 1512, 1514 can comprise one or more rectilinear, curvilinear, or other bends in the shaft 1518. As is illustrated in FIG. 15 the first cam portion 1512 is located adjacent a first side of the pivot and the second cam portion 1514 is located adjacent a second side of the pivot. The second cam portion 1514 can comprise a portion of the remote-most end or cam (not shown but similar to the remote-most end or cam 20 of FIG. 3) of the shaft 1518. First 1520 and second 1522 cam contact surfaces are located on a bottom surface of the second bristle holder 1508. As is the case with all the described embodiments, the amplitude or height of the bends or eccentricities that make up the first and second cam portions 1512, 1514 are large enough reach the related cam contact surface(s) and to drive the second bristle holder a desired distance toward, into, across or along a toothbrush users teeth. Changing the distance between the apexes and the pivot point can vary the required amplitude or height. Changing the distance between the apexes and the pivot point may affect a required or desired torque delivered by the motor 819. As the motor 819 of the enhanced toothbrush 810 rotates the shaft 1518, the first cam portion 1512 comes into contact with the first cam contact surface 1520 and drives or lifts (relative to the figure) a first end 1530 of the second bristle holder 1508 causing the first end 1530 to rock or move about the pivot 1510 in a direction away from the head portion 816 and toward the teeth of a toothbrush user (not shown). This action lowers a second end 1526 of the second bristle holder back toward the head portion 816. As the shaft 1518 continues to rotate, the first cam portion 1512 becomes disengaged with the first cam contact surface 1520 and the second cam portion 1514 engages the second cam contact surface 1522. The second cam portion 1514 drives or lifts (relative to the figure) the second end 1526 of the second bristle holder 1508 causing the second end 1526 to rock or move about the pivot 1510 in a direction away from the head portion 816 and toward the teeth of the toothbrush user. This action lowers a first end 1530 of the second bristle holder back toward the head portion 816. During use, as the first and second cam portions 1512, 1514 alternately come in contact with the first and second cam contact surfaces 1520, 1522, bristles of the second bristle holder 1508 are urged against teeth of the user with varying degrees of force. Preferably, bristles of the second bristle holder 1508 are urged between the teeth of the user to provide a cleaning and flossing function. As the rocking or pivoting motion is repeated (as the shaft 1518 continues to rotate), a flossing or deep cleaning motion is provided that is distinct from and complimentary to the motion provided by the first bristle holder 814.

Figure 16:
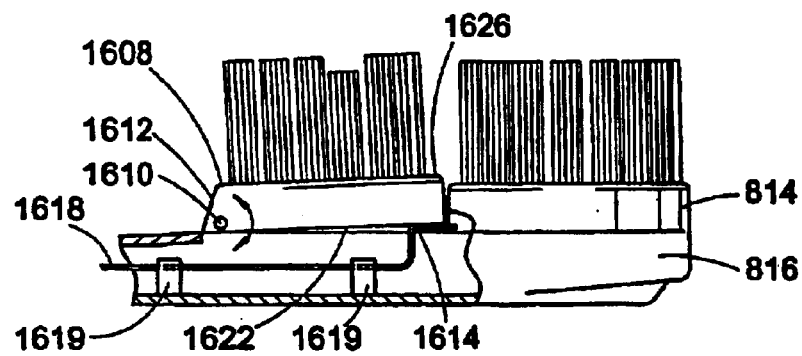
FIG. 16 is a partial sectional view taken along B—B in FIG. 8 of a seventh embodiment of a toothbrush head.

Referring to FIG. 16, in a seventh embodiment of the enhanced toothbrush 810 a second bristle holder 1608 is movably mounted to the toothbrush head 816 with a pivot 1610, which can be provided in the form of a pin or of a hinge installed at a transverse axis of the second bristle holder 1608. In one embodiment, the second bristle holder 1608 pivots about a pin, which is anchored in the sidewalls of the toothbrush neck at the midpoint of the second bristle-holder 1608. The transverse axis is, for example, adjacent to a first end 1612 of the second bristle holder 1608. The second bristle holder 1608 is separately driven in a vibratory, swinging, pivoting or rocking motion by a cam 1614 included on a driving shaft 1618. Optionally, the shaft is supported by shaft supports 1619. The shaft supports may include C or U shaped portions (not shown) that are: operative to receive and snap around the shaft. Other means for retaining a shaft in a support are known in the art. The cam 1614 may be a portion of a remote-most end of the shaft 1618 (not shown but similar to the remote-most end or cam 20 of FIG. 3). The cam 1614 can comprise one or more bends in the shaft 1618. For example, the bends can be rectilinear, curvilinear or other kinds of bends. A cam contact surface 1622 is located on a bottom surface of the second bristle holder 1608 adjacent to a second end 1626 thereof. As the motor 819 of the enhanced toothbrush 810 rotates the shaft 1618, the cam 1614 comes into contact with the cam contact surface 1622 and drives or lifts (relative to the figure) the second end 1626 of the second bristle holder 1608 causing the second end 1626 of the second bristle holder 1608 to rock or move about the pivot 1610 in a direction away from the head portion 816 and toward the teeth of a toothbrush user (not shown). As the shaft 1618 continues to rotate, the cam 1614 becomes disengaged with the cam contact surface 1622. During use, as the cam 1614 comes in contact with the cam contact surface 1622, bristles of the second bristle holder 1608 are urged against teeth of the user with a varying degree of force. Preferably, bristles of the second bristle holder 1608 are urged between the teeth of the user to provide a cleaning and flossing function. As the cam disengages with the contact surface 1622, bristles pressing against the teeth of the user urge the second bristle holder away from the users teeth and back toward the head portion 816. As this swinging or pivoting motion is repeated (as the shaft 1618 continues to rotate), a flossing or deep cleaning motion is provided that is distinct from, and complimentary to, the motion provided by the first bristle holder 814.

Figure 17:
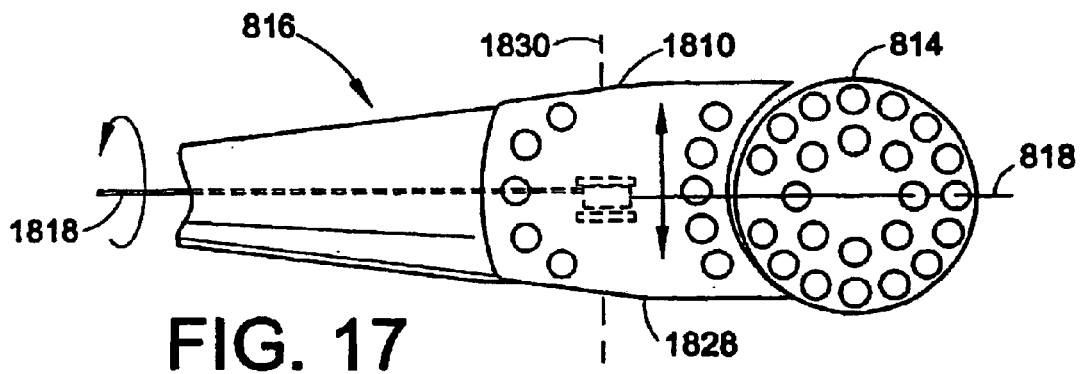
FIG. 17 is a bottom view of a head portion of a ninth embodiment of a toothbrush.
Figure 18:
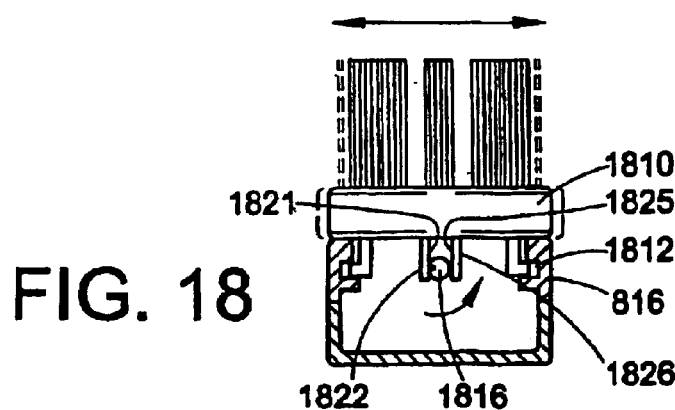
FIG. 18 is a partial sectional view taken along B—B in FIG. 8 of the ninth embodiment of a toothbrush head.

Referring to FIG. 17 and FIG. 18, in a eighth embodiment of the enhanced toothbrush 810 a second bristle holder 1810 is movably mounted in slots 1812 in the toothbrush head 816 and separately driven in a reciprocating or translating, transverse motion within the slots 1812 by a cam 1816 included on a driving shaft 1818. The cam 1816 can comprise an appropriately shaped bead placed over or molded and fixedly secured to the shaft 1818. For example, the bead is shaped as and eccentric cam. Alternatively, the cam can include one or more rectilinear, curvilinear or other kind of bend. First 1822 and second 1826 cam followers depend from a bottom surface of the second bristle holder 1810. The cam followers are, for example, offset from the longitudinal axis 818 of the second bristle holder and straddle or capture the cam 1816. As the motor 819 (see FIG. 8) rotates the shaft 1818, the cam 1816 comes into contact with a surface 1821 of the first cam follower 1822 and drives the first cam follower 1822, and therefore, the second bristle holder 1810 away from a first side 1828 of the head portion 816 along a transverse axis 1830 of the head portion 816. As the shaft 1818 continues to rotate, the cam 1816 becomes disengaged with the first cam follower 1822. The cam 1816 then comes into contact with a surface 1825 of the second cam follower 1826 and drives the second cam follower 1826, and therefore, the second bristle holder 1810 back toward the first side 1828 of the head portion 816. As this back and forth or side to side motion is repeated (as the shaft 1818 continues to rotate), a sweeping motion is provided that is distinct from and complimentary to the motion provided by the first bristle holder 814.

Figure 19:
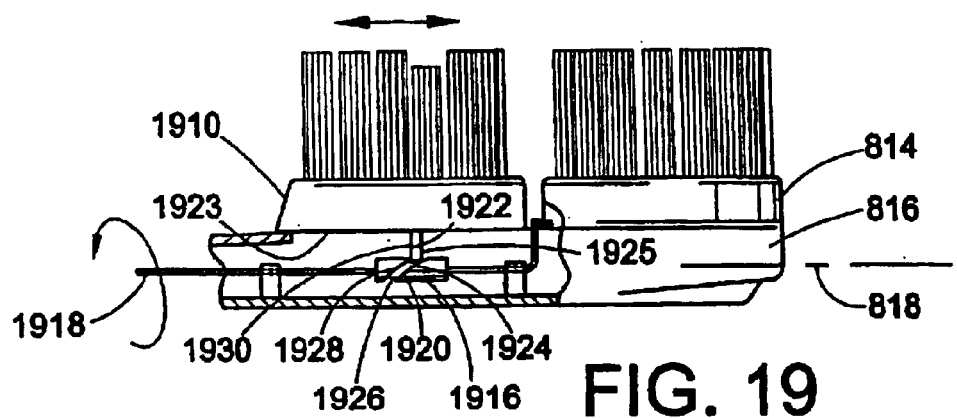
FIG. 19 is a partial sectional view taken along B—B in FIG. 8 of a tenth embodiment of a toothbrush head.

Referring to FIG. 19 in a ninth embodiment of the enhanced toothbrush 810 a second bristle holder 1910 is movably mounted in slots (not shown) in the tooth head 816 and separately driven in an 1918. The cam 1916 can comprise a shaped bead, with an appropriate configuration, placed or molded over and firmly secured to the shaft 1918. The cam around a circumference of the bead and spirals about a longitudinal axis of the bead. For example, the longitudinal axis coincides with the shaft 1918. A cam follower 1922 depends from a bottom surface 1923 of the second bristle holder 1910. The cam follower 1922 is slidingly received within the spiral groove 1920. As motor 819 of the enhanced toothbrush 810 rotates the shaft 1918, a first surface 1924 of the spiral groove 1920 comes into contact with a first surface 1925 of the cam follower 1922 and drives the cam follower 1922, and therefore, the second bristle holder 1910 away from the first bristle holder 814 along the longitudinal axis 818 of the head portion 816. As the shaft 1918 continues to rotate, the cam follower 1922 reaches 1922 reaches an apex 1926 of the spiral groove 1920 and the first surface 1924 of the spiral groove 1920 becomes disengaged with the first cam surface 1925. A second surface 1928 of the spiral groove 1920 then comes into contact with a second surface 1930 of the cam follower 1922 and drives the cam follower 1922, and therefore, the second bristle holder 1910 back toward the first bristle holder 814. As this back and forth motion is repeated (as the shaft 1918 continues to rotate), a scrubbing motion is provided that is distinct from and complimentary to the motion provided by the first bristle holder 814. Optionally cam 1916 is eccentrically mounted on the shaft 1918 and the longitudinal axis of the bead or cam 1916 does not coincide with the shaft 1918. In this case, if the cam follower 1922 is made long enough to ride on the bottom of the spiral groove 1920, a lifting or vertical pulsing force is provided to the second bristle holder as the eccentrically mounted came is rotated by the shaft. Alternately, or additionally, the depth of the groove is varied. The variation in depth provides lifting or vertical pulsing forces to the cam follower and therefore to the second bristle holder. The spiral groove may be replaced with a groove that cycles back and forth along the longitudinal axis of the bead several times as it circles the bead. This sort of groove can be used to increase the reciprocating frequency of the second bristle holder.

Figure 20:
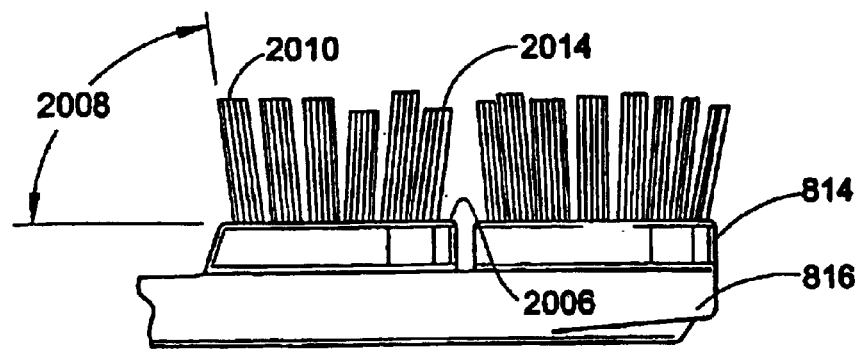
FIG. 20 is a side view of a toothbrush showing a first exemplary alternate bristle arrangement.
Figure 21:
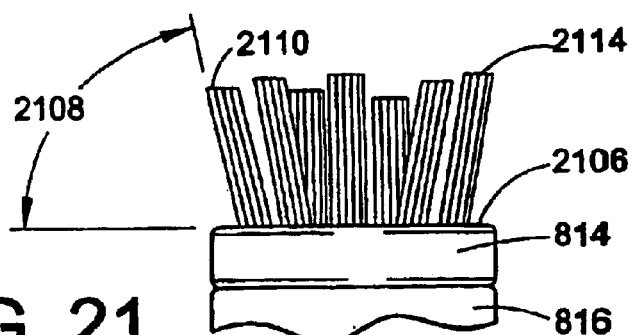
FIG. 21 is an end view taken along D—D of FIG. 8 showing a second exemplary bristle arrangement.

With the embodiments of the present invention have been illustrated for simplicity with bristles, which extend in a direction substantially perpendicular to the longitudinal axis 818 and the surface (for example see 1115 of FIG. 11) of the bristle holders, it is contemplated that the bristles might be arranged differently to complement or further enhance the motions of the first and/or second bristle holders. Referring to FIG. 20, some or all of the bristles might extend in a direction which forms an acute angle 2008 to a surface 2006 of the bristle holder and extends in a direction toward or away from the handle, such as shown by way of example in FIG. 20 with respect to bristles 2010 and 2014 respectively. Referring to FIG. 21, in another embodiment, some of the bristles might extend outwardly away from head, in another direction, again forming an acute angle 2108 with respect to the surface of the bristle holder, as shown by way of example in FIG. 21 with respect to bristles 2110 and 2114. Massaging bristles or bristles of varying height might also be used, such as described in U.S. Pat. Nos. Des. 330,286, Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910; the substances of which are incorporated herein by reference.

The described embodiments have been described with certain words and phrases that attempt to describe certain motions. Motion can either be constant or vibratory. One example of a constant motion is simple rotation where an element angularly moves in a single direction (e.g., a bristle holder which only rotates clockwise or swivels clockwise in a cone like envelope) or translates in a single direction.

Vibration is any periodic movement having repeated cycles. Vibratory motion can have one or more frequencies and amplitudes. Vibratory movement which is substantially linear is referred to herein as a reciprocating motion. Reciprocating motion can occur in a number of directions, such as substantially horizontal, substantially vertical (i.e., a lifting or pulsating motion), and combinations thereof. Vibratory movement which is substantially rotational in nature is referred to herein as an oscillatory or pivoting motion.

Because most motions can be complex in nature (i.e., include elements of other types of motion), the use of the above-described terms herein can include other motions, unless stated otherwise (e.g. reciprocates only), in addition to the basic or primary motion described by the term. So, for example, a motion which is described herein as reciprocating may also include other vibratory or constant movements even though the primary movement is reciprocatory in nature.

Figure 22:
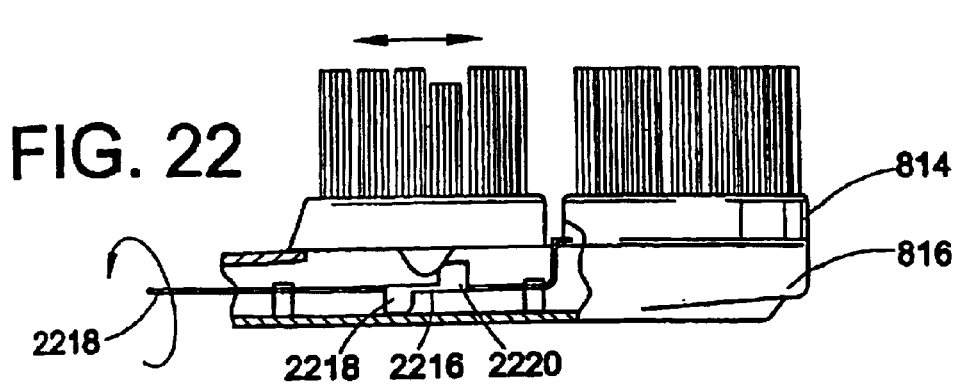
FIG. 22 is a partial sectional view taken along B—B in FIG. 8 of a second implementation of the fifth embodiment showing an alternate cam design.

The invention has been described with reference to particular embodiments. Modifications and alterations will occur to others upon reading and understandings this specification. For example, while certain have been described as comprising bends in a shaft and other cams have been described as including appropriately shaped beads secured to a shaft, the cams are not limited to the suggested form. Indeed, bends may be substituted for beads and beads may be substituted for bends. For example, FIG. 22 illustrates a tenth embodiment that is similar to the fifth embodiment illustrated in FIGS. 13 and 14. However, in the tenth embodiment the cam 2216 is formed as an appropriately configured complex bead fixedly placed or co-molded over the shaft 2218. The cam 2216 provides shapes 2218, 2220 with surfaces that serve an equivalent purpose to the arcuate bends 1319, 1320 described in reference to the fifth embodiment. Where first and second cam portions or surfaces are described or referenced, the portions or surfaces can be considered to be or implemented as separate cams. Where cams or cam portions are illustrated with one eccentricity or bent shape, multiple eccentricities or bent shapes may be included. Each added eccentricity or bent shape would increase the frequency with witch the related bristle holder vibrates, pulses, pivots, swivels, rocks, oscillates, reciprocates or translates. Additionally, where multiple eccentricities are included, they may be of varying amplitude, thereby providing varying bristle holder movement amplitudes. It is intended that all such modifications and alternations are included insofar as they come within the scope of the appended claims or equivalents thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush, comprising:
   a handle having a motor disposed therein;
   a head having a longitudinal axis, the head having a first bristle holder with a plurality of bristle tufts and a second bristle holder with a plurality of bristle tufts, the second bristle holder having an end portion, each of the bristle tufts of the first and second bristle holders having a base end connected to its respective bristle holder and an opposite free end;
   a neck disposed between the handle and the head;
   wherein the motor is operatively connected to the first bristle holder to oscillate the first bristle holder about a first axis passing through the first bristle holder generally perpendicular to the longitudinal axis of the head; and
   wherein the motor is operatively connected to the second bristle holder to oscillate the second bristle holder about a second axis transverse to the longitudinal axis of the head, wherein the base ends of the tufts of the second bristle holder move in unison and in the same direction with the free ends thereof, and wherein the second axis is at the end portion of the second bristle holder.

2. The electric toothbrush of claim 1, wherein the end portion of the second bristle holder is located adjacent the neck.

3. The electric toothbrush of claim 1, wherein the toothbrush further comprises a shaft having a longitudinal axis and operatively connected to the motor, wherein the shaft engages the first and second bristle holders.

4. The electric toothbrush of claim 3, wherein the shaft further comprises a cam, and wherein the engagement between the shaft and the second bristle holder occurs between the cam and the second bristle holder.

5. The electric toothbrush of claim 3, wherein the shaft further comprises a cam, and wherein the engagement between the shaft and the first bristle holder occurs between the cam and the first bristle holder.

6. The electric toothbrush of claim 5, wherein the first bristle holder has a slot that captures the cam such that the engagement between the cam and the first bristle holder occurs between the cam and the slot.

7. The electric toothbrush of claim 6, wherein the cam is at a remote-most end of the shaft.

8. The electric toothbrush of claim 3, wherein the shaft further comprises a cam, and wherein the engagement between the shaft and the first and second bristle holders occur between the cam and the first and the second bristle holders.

9. The electric toothbrush of claim 8, wherein the cam is secured to the shaft.

10. The electric toothbrush of claim 3, wherein the shaft is rotatable.

11. The electric toothbrush of claim 3, wherein shaft completely passes under the second moving bristle holder and does not completely pass under the first bristle holder.

12. The electric toothbrush of claim 1, further comprising a gap between the first bristle holder and the second bristle holder.

13. The electric toothbrush of claim 1, wherein the first axis is surrounded by the plurality of bristles of the first bristle holder.

14. The electric toothbrush of claim 1, wherein the plurality of bristle tufts of the second bristle holder differ in height.

15. The electric toothbrush of claim 14, wherein the second bristle holder further has a top surface, and wherein at least one of the bristle tufts of the second bristle holder forms an acute angle with the top surface of the second bristle holder.

16. The electric toothbrush of claim 15, wherein the at least one of the bristle tufts of the second bristle holder is angled away from the neck.

17. The electric toothbrush of claim 16, wherein the at least one of the bristle tufts of the second bristle holder is angled toward the neck.

18. The electric toothbrush of claim 1, wherein the head directly supports the first and second bristle holders.

19. The electric toothbrush of claim 1, wherein the first bristle holder further comprises a top surface and wherein some of the plurality of bristle tufts of the first bristle holder form an acute angle with the top surface of the first bristle holder.

20. The electric toothbrush of claim 19, wherein the plurality of bristle tufts of the first bristle holder differ in height.

* * * * *